United States Patent [19]

Stern

[11] Patent Number: 5,382,164
[45] Date of Patent: Jan. 17, 1995

[54] METHOD FOR MAKING DENTAL RESTORATIONS AND THE DENTAL RESTORATION MADE THEREBY

[76] Inventor: Sylvan S. Stern, 14720 Loretta Pl., Oak Park, Mich. 48237

[21] Appl. No.: 97,956

[22] Filed: Jul. 27, 1993

[51] Int. Cl.⁶ .................. A61C 5/10; A61C 11/00
[52] U.S. Cl. ........................... 433/223; 433/213
[58] Field of Search ............... 433/218, 223, 213, 214

[56] References Cited

U.S. PATENT DOCUMENTS

| | | | |
|---|---|---|---|
| 3,861,044 | 1/1975 | Swinson, Jr. | 433/213 X |
| 4,324,546 | 4/1982 | Heitlinger et al. | 433/213 |
| 4,611,288 | 9/1986 | Duret et al. | 433/213 |
| 4,695,254 | 9/1987 | Herrell | 433/213 |
| 5,092,022 | 3/1992 | Duret | 29/160.6 |

OTHER PUBLICATIONS

Siemens® CEREC Computer Reconstruction (Brochure).
Sopha® Bioconcept, Inc. (Brochure).

*Primary Examiner*—Paul J. Hirsch
*Assistant Examiner*—Nicholas D. Lucchesi
*Attorney, Agent, or Firm*—Reising, Ethington, Barnard, Perry & Milton

[57] ABSTRACT

The present invention relates to a method of making dental restorations and the dental restoration made by the method comprising temporarily repairing a tooth area to be restored to a desired final shape, taking a first impression of the tooth area to be restored, preparing the tooth to be restored and forming a second impression within first impression with material that is non-adherent to the first impression material. The first impression and the second impression are separated. The second impression is scanned to electronically obtain an image of the final restoration.

12 Claims, 2 Drawing Sheets

FIG-2
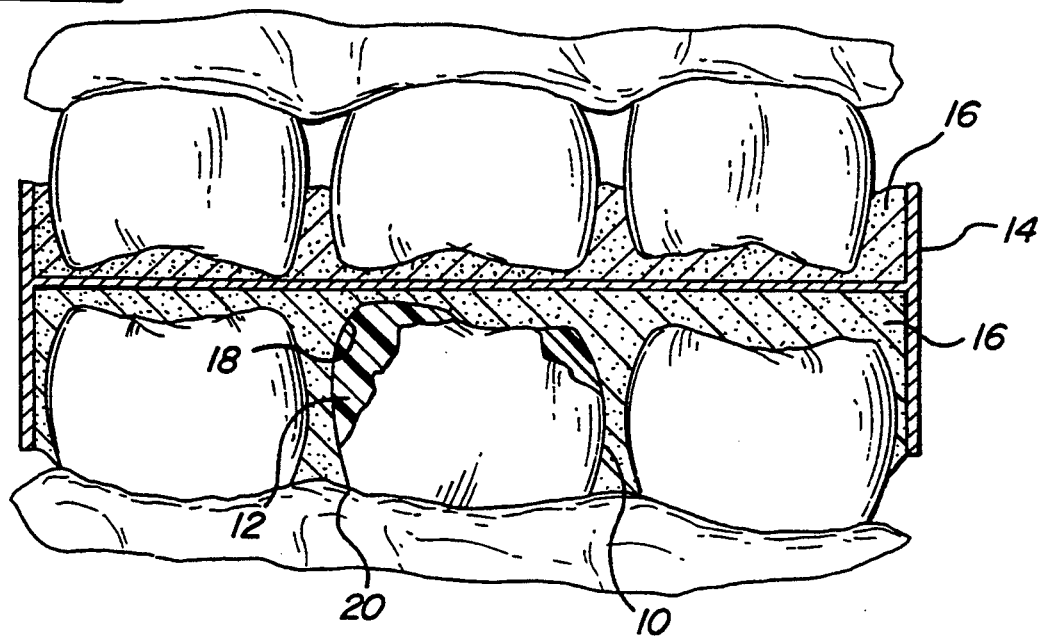
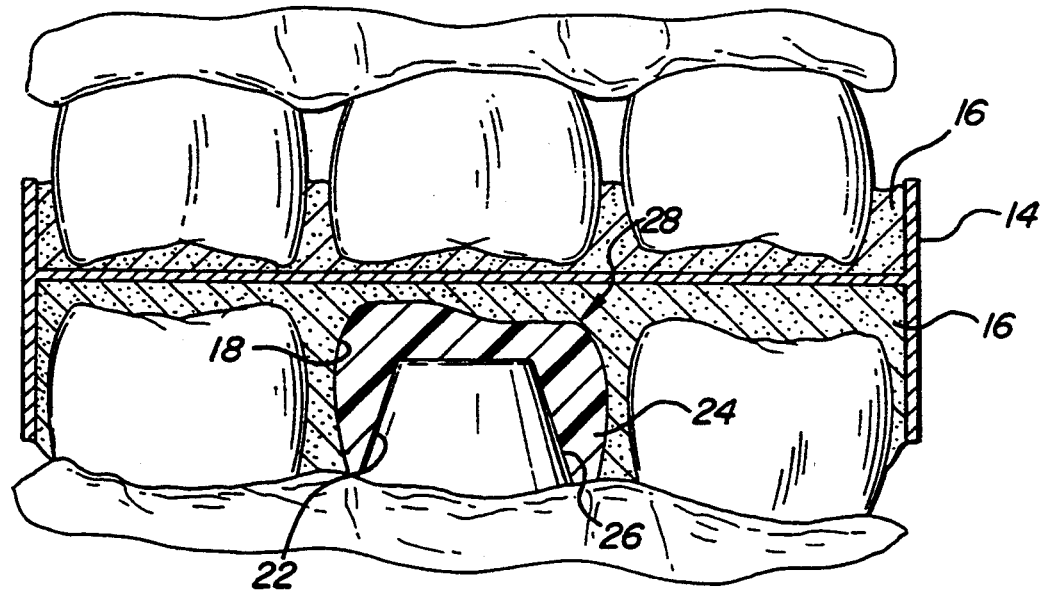
FIG-3
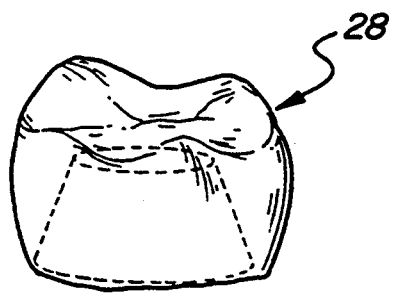
FIG-4

METHOD FOR MAKING DENTAL RESTORATIONS AND THE DENTAL RESTORATION MADE THEREBY

TECHNICAL FIELD

This invention relates to a method of making dental restorations and the restoration made thereby.

BACKGROUND OF THE INVENTION

Making dental restorations is important in many situations. First, human teeth are subject to naturally occurring breakdowns such as decay and wear. Decay will normally be corrected through semi-permanent means such as fillings and the like. However, after numerous years, decay can reach a point where restoration of the tooth through an inlay, onlay or crown becomes necessary.

Another situation in which a dental restoration is important is where an accident involving a blow to the mouth results in chips, cracks and/or breaks of the tooth. In these situations, the patient not only requires relief from the discomfort associated with the dental injury but also desires to have the injured tooth or teeth returned to their pre-accident appearance. Once again, a restoration in the form of an inlay, onlay or crown is necessary.

Using conventional means of preparing restorations is often time consuming for both the dentist and patient. Generally, more than one visit by the patient is necessary. The first visit entails preparing the tooth or teeth for restoration and fitting the prepared tooth/teeth with a temporary substitute until delivery of the final restoration. During this visit, final impression is taken and a working model is prepared with individual teeth separated and indexed to be able to be precisely reassembled. The model teeth are carefully trimmed to indicate the margins of the final restoration. This trimming preferably is done by the dentist. The model is then used by a dental lab technician who is usually located in a remote dental laboratory to fabricate the final restoration. This procedure usually takes two to three weeks to be finished, at least in part due to the time involved in firing and casting porcelain. Porcelain is a material commonly used in making dental restorations. There are multiple steps and each step introduced inaccuracies.

Once the dentist receives the final restoration back in the office from the laboratory, the patient returns for another appointment. This appointment involves removing the temporary substitute and then adjusting and permanent placement of the final restoration. During this appointment final adjustments to accommodate chewing motions of opposing teeth are performed by the dentist in the patient's mouth and then the restoration has to be polished again.

Communication with a lab technician at a remote lab frequently is imperfect and the restoration received is not exactly what was expected. This requires repeating certain steps which were already taken resulting in frustration for both dentist and patient.

Furthermore, certain procedures, such as fitting a crown under a partial denture clasp that already exists is extremely inaccurate using any existing method. In fitting a crown under a partial denture clasp, the dentist is required to spend a considerable amount of time in contouring and fitting the restoration in regard to the other surrounding and opposing teeth. This problem is resolved with the method being presented. Besides the time involved, when a crown does not exactly fit the existing partial denture clasp, the partial denture will not seat properly and this in turn will disrupt the patient's occlusion and lead to further pathology.

Recently, computer reconstruction of dental restorations has become commercially feasible. Generally, these systems involve an optical reader which generates a computer-read signal. Siemens ® and Sopha ® CAD/CAM both have commercially available systems which optically read tooth areas in conjunction with dental reconstruction. Sopha ® uses the optical impression system as disclosed in U.S. Pat. No. 4,611,288 to Duret et. al.

The use of optical impression systems greatly reduces the amount of time involved in preparing a restoration as compared with conventional methods, but still has several drawbacks.

The Siemens ® reconstruction system eliminates the requirement of a model by using optical impressions made by a specially designed camera. The camera is used in the mouth to read the contour of the tooth. Using the camera in the mouth results in a certain amount of inaccuracy due to moisture in the mouth and on the tooth surface, use of an imaging powder over the prepared tooth, the presence of the tongue and difficulty in manipulating the camera in areas further back in the mouth. In addition, this method does not record the opposing tooth and cannot fit a restoration to a partial denture clasp that already exists. As a result, the restoration may require extensive contouring by the dentist before the restoration is properly fitted. As previously discussed, contouring is a time consuming step.

The Sopha Bioconcept ® CAD/CAM is different from the Siemens ® system in that it requires a working model before the restoration is carried out. This added step increases the time to make and the expense of the final restoration. In addition, the Sopha Bioconcept ® system does not record the opposing teeth. Rather, this system fabricates a tooth with a textbook morphology and the dentist makes modifications on a computer screen and the model and in the mouth to customize the final design. The Sopha Bioconcept ® cannot fit a crown to a partial denture clasps that already exists.

Like the Sopha ® system, U.S. Pat. No. 4,324,546 to Heitlinger et. al. also requires a model. This patent describes a method of manufacturing dentures, wherein a prepared tooth stump is reproduced as a working model. The reproduction of the tooth stump is accomplished electro-optically to produce signals which are fed through a computer which in turn operates a milling machine. This, like the Sopha ® method, entails the use of a working model.

SUMMARY OF THE INVENTION

The present invention relates to a method of making dental restorations including the steps of taking a first impression of the tooth area to be restored. The tooth is then prepared to be restored and a second impression is formed within the first impression. The first and second impression are made from materials that are non-adherent to each other. The first impression is separated from the second impression and the second impression is scanned to electronically obtain an image of the final restoration, without the use of a model.

It is the goal of the present invention to eliminate the need for the extensive occlusal contouring of the final restoration which is required with the use of an optical impression system in making dental restorations without consideration of opposing teeth. It is also a goal of the present invention to eliminate the requirement of a working model such as is required in the Sopha ® system and conventional lost wax technique. Furthermore, it is also a goal to be able to fabricate customized designs to fit existing prosthetic appliances already being worn by a patient, predictably and accurately.

FIGURES IN THE DRAWINGS

FIG. 2 is a drawing of the first impression of the full shaped tooth that was temporarily restored to desired final shape.

FIG. 3 is the schematic drawing of the second impression within the first impression over the tooth cut for a crown.

FIG. 4 is a drawing of the second impression in the shape of a crown after it has been separated from the first impression.

DETAILED DESCRIPTION OF THE INVENTION

Figure 1:
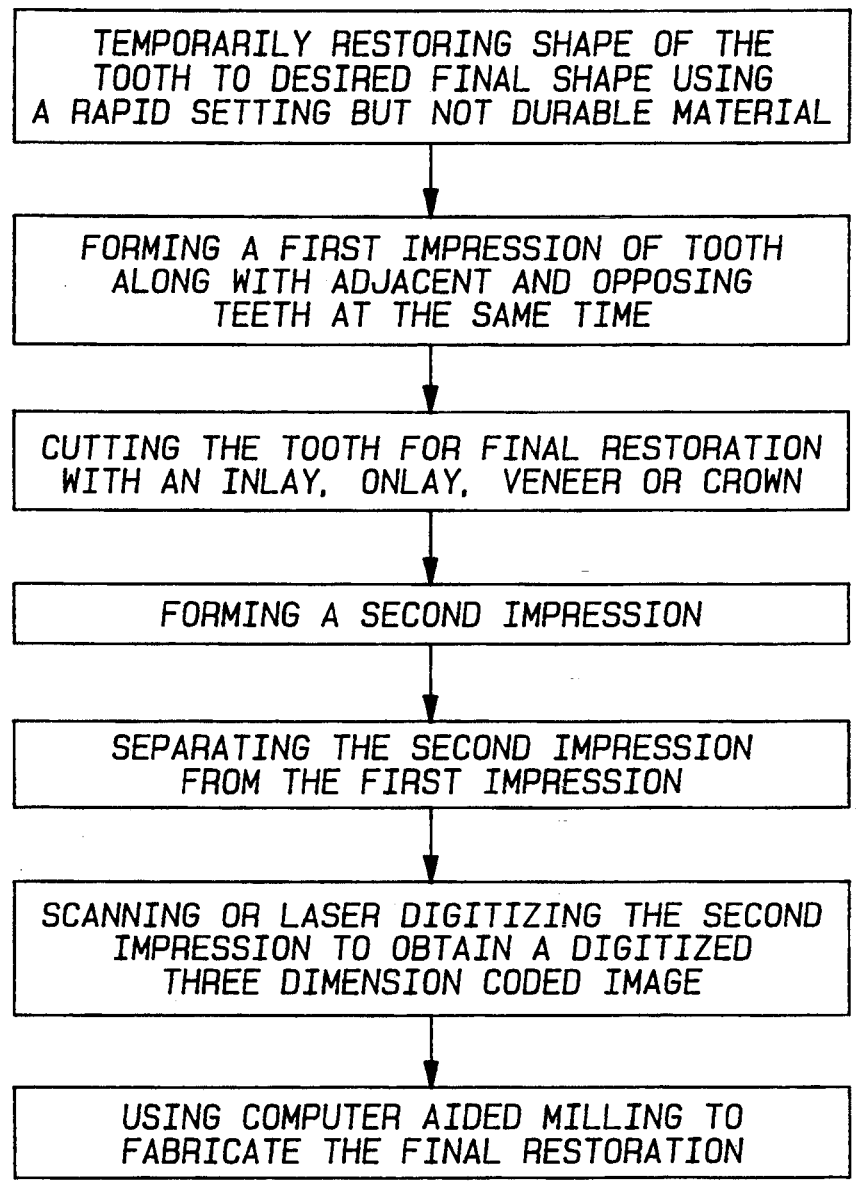
FIG. 1 is the schematic diagram showing the steps utilized in the method of the present invention.

The method of the present invention is schematically shown in FIG. 1. The first step in making the dental restoration is temporarily repairing, intraorally, any fractured areas or malformations of the tooth 10. The repair 12 places the tooth 10 in the desired shape of the final restoration. This can be accomplished with various materials, which are not necessarily strong enough for long term wear. A cement filling material such as GC Miracle Mix, available from GC Corporation, Tokyo, Japan is a good example of composite restorative material. Another acceptable material is Kerr Herculite ®. The next step is to take an impression of the tooth area to be restored. This impression is made by using an impression tray 14 designed to take opposing teeth at the same time (preferably Tri-Bite ® trays available from Direct Dental Service in Lansing, Mich.). These trays 14 come in various sizes to accommodate any location in a mouth. A hydrophilic elastomeric material 16 made from a polyvinyl siloxane, preferably Reprosil Quixx TM Putty and light body wash is placed in the tray 14. Reprosil Quixx TM Putty is available from the L.D. Caulk Division, Dentsply International Inc. in Milford, Del. The tray 14 along with the elastomeric material 16 are placed into the patient's mouth over the area of the tooth 10 that will be restored (FIG. 2). The tray 14 is left in the mouth until the material sets, which generally takes about 5 minutes. The tray 14 is then removed from the mouth and the resulting impression is called the first impression 18.

Next, using a medium grit diamond chamfer bur such as Brasseler ® 5897K in a high speed drill, the cervical margin 20 is shaved about 1 millimeter to prevent a build-up of hydraulic pressure during a later procedure. Brasseler ® instruments are available from Brasseler USA in Savannah, Ga.

The tooth 10 is prepared and soft wax (dental utility wax) is used to block out interproximal undercuts and trimmed as needed.

A second impression 22 is then taken. The second impression 22 is preferably made utilizing a low-shrinkage low heat releasing acrylic 24 wherein the acrylic is an alkyl methacrylate, including Aristocrat HTC ® self cure resin available from HealthCo Inc. of Boston, Mass. The materials used in the first impression and second impression are non-adherent to each other. Alternatively, the second impression 22 may be made from a material that does have a tendency to adhere to the first impression material 16. In this event, a separating material such as Modern Foil available from Modern Materials of St. Louis, Mo. is used to coat the first impression 18 to prevent adherence between the first 18 and second 22 impression. The second impression 22 is made by mixing the second impression material 24 to a free flowing consistency and injecting it with an impression syringe around the prepared tooth 26. In the event non-adherent material such as the Aristocrat HTC ® is used, the material is placed directly into the first impression 18. If an adherent material is used, the separating material is applied to the first impression 18 and allowed to dry prior to filling the first impression with the second impression material 24 in the site of the prepared tooth. The first impression 18 now containing the second impression material 24 in the area of the prepared tooth is then placed over the tooth 26 making certain to seat it to fit over the adjacent teeth (FIG. 3). The patient is then directed to bite down. The first impression 18 is thus seated in the exact position it was in when it recorded the prepared tooth 10 before it was cut. As a result, the second impression material 24 fills in the gap that resulted from cutting the tooth. The exact shape of the prepared tooth 26 structure is thus reproduced in the second impression material 24 which is called for our purposes the second impression mold, generally shown at 28. The second impression mold 28 has the shape of the final restoration but in a non-durable material. The second impression mold 28 has the external shape of the precut tooth 10 and the internal shape of the cut tooth 26. It is trimmed intraorally more rapidly than final restoration material because it is much softer.

The second impression material 24 is allowed to harden and then the tray 14 is removed from the mouth. The Aristocrat HTC ® hardens in about 7 minutes and the tray 14 with the first 16 and second impression 24 material may be removed from the mouth. The second impression mold 28 will be found either on the tooth 26 or inside the first impression material 24. Its easily popped out of the first impression 18 or lifted off of the tooth 26 at this time. After isolating (FIG. 4) the second impression mold 28 any flash of material is trimmed off. Using 10× magnification and a high speed drill with a finishing bur such as Brasseler ® H48L the margins are refined to a clean finishing line. It is replaced over the tooth 26 and the occlusion is adjusted in the mouth. The second impression mold 28 is shaped to accommodate chewing motions and to appear pleasing esthetically. The second impression mold 28 is removed from the mouth and scanned with a laser or optical scanner designed to digitize three dimensional surfaces and to obtain an image of the final restoration. This electronically generated image is then used by a computer to mill the final restoration. The final restoration is a duplicate of the second impression mold 28 but is made from a material which has been designed to be used for esthetic restorations such as Dicor MCG ® available from either Corning or Dentsply. This material is already in use clinically and has been shown to function very well. The final restoration can also be made from various metals or ceramics or other restorative materials, too. This finished restoration is now ready to be cemented in the patient's mouth, using conventional dental cementing procedures.

If a partial denture was worn during the first impression 18 and was incorporated into the first impression and left inside, the second impression 22 automatically precisely fits the partial denture clasp in a functional position that accommodates the patient's chewing pressure. This is because the patient was biting down with the partial denture in place during both impressions.

The above description is for making a single restoration. In order to replace missing teeth with a fixed bridge a modification of the above method can be used. This modification requires making a plaster model of the patient's teeth. The shape of the missing tooth or teeth is initially formed on the plaster model using a composite material. This is a non-durable replacement. Bonding agents and small pins are then used to place the non-durable replacement tooth in the mouth. Final shaping of the nondurable replacement is done intraorally. Next, the procedures enumerated above for creating a dental restoration are followed. The first impression is made of the tooth and adjacent teeth. Then the teeth adjacent to this replacement are shaped for crowns and the replacement tooth just formed is removed from the mouth. Next, the second impression is taken to obtain the bridge form for computer reproduction. An all metal gold bridge can thus be formed. Also a metal substructure for conventional metal/ceramic bridges can also be formed. In this case, a ceramist can apply a ceramic coating over the metal substructure using conventional methods. The "outer surface" should be reduced by approximately one to two millimeters to provide space for porcelain. It has been found that one and one half millimeters is preferred. This method still reduces the time needed and the cost associated with the form of bridges. Further, the bridge and teeth are less subject to distortion while being fabricated.

There are many benefits of the method described. First, there is no need to pour models, including using an articulator to relate the opposing teeth, separate the teeth, and then either form the restoration in wax or porcelain using conventional means or optically scanning the model.

Efficiency is also another benefit resulting from the present material. The time involved in making castings or firing porcelain in an oven is eliminated. Using the second impression mold 28 for scanning purposes outside of the mouth eliminates many of the drawbacks associated with intraoral optical impressions. For example, the inaccuracies resulting from moisture present along the tooth surface, difficulty in manipulating the camera in areas further back in the mouth, or the fact that teeth may be stained by old restorations and get misread by optical imaging equipment are not factors in laser scanning of the second impression mold 28.

The dentist has much more control of the shape of the final restoration then when depending on another individual to fabricate a restoration without the benefit of looking at the whole face, or of a machine programmed to fabricate ideal tooth shapes without any consideration of the individual case.

Dentists can see the final shape in the mouth and no longer need to wonder how the modifications made on the computer screen during the designing the restoration with computer aided milling is going to appear in the mouth.

Patients do not require temporary restorations that need to be lasting many weeks which potentially fracture in the interim and certainly cause gingival irritation and possibly cause shifting of the teeth in the interim.

The ability to fit restorations to existing prostheses precisely and reliably.

In addition, the second impression shape incorporates in exact detail the relationship of opposing teeth with all jaw movements taken into account. All these factors yield a final restoration which may be properly fitted with far less contouring required by the dentist. This is time and cost saving to the dentist and the patient.

The invention has been described in an illustrated manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A method of making dental restorations comprising the steps of temporarily repairing a tooth area to be restored to a desired shape of a final restoration, taking a first impression of the tooth area to be restored, preparing the tooth area to be restored for restoration, forming a second impression within the first impression with material that is non-adherent to the first impression, separating the first impression from the second impression and optically scanning the second impression to electronically obtain an image of the final restoration.

2. A method of making dental restorations according to claim 1 further comprising the steps of adjusting the margins after forming the first and second impressions.

3. A method of making dental restorations according to claim 1 further comprising using a computer to generate at least one graphic representation of the final restoration.

4. A method of making dental restorations according to claim 1 further comprising using computer controlled milling to create the final restoration.

5. A method of making dental restorations according to claim 1 wherein the second impression is a replica of the tooth area to be restored in its original form and as prepared for restoration.

6. A method of making dental restorations according to claim 1 wherein the first impression is made with an elastomeric medium.

7. A method of making dental restorations according to claim 6 wherein the elastomeric medium is a polyvinyl siloxane.

8. A method of making dental restorations according to claim 1 wherein the second impression is made from an acrylic substance.

9. A method of making dental restorations according to claim 8 wherein the acrylic substance is an alkyl methacrylate.

10. A method of making dental restoration comprising the steps of temporarily a repairing tooth area to be restored to desired shape of a final restoration, taking a first impression of the tooth area to be restored with an elastomeric medium comprising, polyvinyl siloxane, preparing the tooth area to be restored for restoration, forming a second impression with an acrylic like substance comprising alkyl methacrylate, the second impression being formed within the first impression, separating the first impression from the second impression, optically scanning the second impression for creating an image of the restoration, using a computer to generate a graphic representation of the restoration, and using computer controlled milling to create the restoration.

11. A method of making dental restorations comprising the steps of temporarily repairing a tooth area to be restored to a desired shape of a final restoration, taking a first impression of the tooth area to be restored, preparing the tooth area to be restored for restoration, coating the first impression with a separating material, allowing the separating material to dry, forming a second impression within the first impression, separating the first impression from the second impression and optically scanning the second impression to electronically obtain an image of the final restoration.

12. A method of making a fixed bridge for replacing missing teeth by forming a plaster model of a patient's teeth including missing teeth, using the model for forming the shape of the missing teeth with composite material thereby yielding a temporary restoration, placing the temporary restoration of the missing teeth in the patient's mouth, forming a first impression of the temporary restoration, preparing teeth adjacent to the temporary restoration for final restoration, removing the temporary restoration from the mouth, taking a second impression of the area where the temporary restoration was located including the adjacent teeth to obtain the form for computer reproduction of the fixed bridge.

* * * * *